US00RE38119E

(19) United States
(12) Reissued Patent
Mower

(10) Patent Number: US RE38,119 E
(45) Date of Reissued Patent: May 20, 2003

(54) METHOD AND APPARATUS FOR TREATING HEMODYNAMIC DISFUNCTION

(75) Inventor: Morton M. Mower, Baltimore, MD (US)

(73) Assignee: Mirowski Family Ventures, LLC, Washington, DC (US)

(21) Appl. No.: 08/547,691

(22) Filed: Oct. 19, 1995

Related U.S. Patent Documents

Reissue of:
(64) Patent No.: 4,928,688
Issued: May 29, 1990
Appl. No.: 07/299,895
Filed: Jan. 23, 1989

U.S. Applications:

(63) Continuation of application No. 10/214,474, filed on Aug. 8, 2002, which is a continuation of application No. 07/890,280, filed on May 29, 1992, now abandoned.

(51) Int. Cl.[7] ..... A61N 1/00
(52) U.S. Cl. ..... 607/9
(58) Field of Search ..... 607/4–28

(56) References Cited

U.S. PATENT DOCUMENTS 3,937,226 A * 2/1976 Funke
4,088,140 A * 5/1978 Rockland et al. ..... 128/419 PG
4,332,259 A * 6/1982 McCorkle, Jr. ..... 128/419 P
4,378,020 A * 3/1983 Nappholz et al.
4,458,677 A * 7/1984 McCorkle, Jr. ..... 128/419 P
4,548,203 A * 10/1985 Tacker, Jr. et al. ..... 128/784
4,624,260 A * 11/1986 Baker, Jr. et al. ..... 607/14
4,774,950 A * 10/1988 Cohen

OTHER PUBLICATIONS

Incomplete Filling and Incoordinate Contraction as Mechanisms of Hypotension during Ventricular Tachycardia in Man, by Joao A. Lima et al., Circulation, vol. 68, No. 5 (1983).*

Aranda, et al., "A New Pacemaker for Simultaneous Biventricular Stimulation . . . ", Clin. Res., 24, 206A.
Befeler, et al., "Programmed Simultaneous Biventricular Stimulation . . . ", Eur. J. of Cardiology, 1979, pp. 369–378.
Haas, et al., "Pacemaker—Induced Cardiovascular Failure", Am. J. of Cardiology, 1974, pp. 295–299.
Lister, et al., "Effect of Pacemaker Site in . . . Heart Block", Am. J. of Cardiology, 1964, pp. 494–503.
Mann, et al., "Entrainment of Ventricular Tachycardia", J. Am. College of Cardiology, 1985, pp. 781–787.
Schlant et al., "Modification of the Law of the Heart: Influence of Early Contracting Areas (P)", Circulation, Supp. III, 1964, pp. III–153 & 154.
Tyers, "Ventricular Stimulation After A–V Block", J. Thoracic and Cardiovas. Sur., 1970, pp. 211–217.
William–Olsson, ". . . Pacemaker Electrode Cite . . . ", J. Thoracic and Cardiovas. Surg., 1963, pp. 618–621.
Zile, et al., "Relaxation and Filling Rates During Asynchrony", J. Am. Coll. Cardiol., 1987, pp. 702–709.

* cited by examiner

*Primary Examiner*—Scott M. Getzow
(74) *Attorney, Agent, or Firm*—Finnegan, Henderson, Farabow, Garrett & Dunner, LLP

(57) ABSTRACT

A method of treating hemodynamic disfunction by simultaneously pacing both ventricles of a heart. At least one ECG amplifier is arranged to separately detect contraction of each ventricle and a stimulator is then activated for issuing stimulating pulses to both ventricles in a manner to assure simultaneous contraction of both ventricles, thereby to assure hemodynamic efficiency. A first ventricle is stimulated simultaneously with contraction of a second ventricle when the first fails to properly contract. Further, both ventricles are stimulated after lapse of a predetermined A-V escape interval. One of a pair of electrodes, connected in series, is placed through the superior vena cava into the right ventricle and a second is placed in the coronary sinus about the left ventricle. Each electrode performs both pacing and sensing functions. The pacer is particularly suitable for treating bundle branch blocks or slow conduction in a portion of the ventricles.

26 Claims, 2 Drawing Sheets

METHOD AND APPARATUS FOR TREATING HEMODYNAMIC DISFUNCTION

Figure 1:
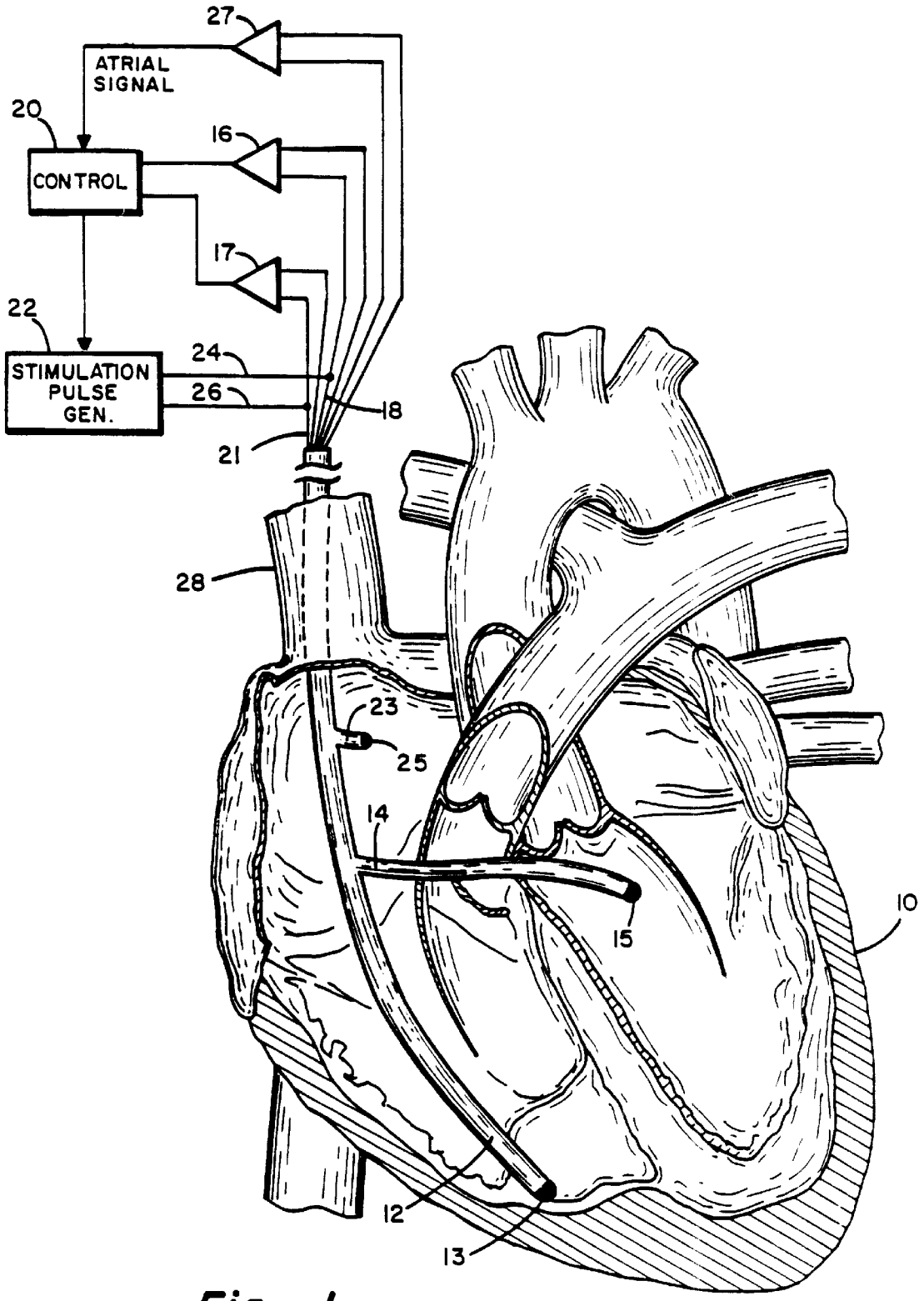

Matter enclosed in heavy brackets [ ] appears in the original patent but forms no part of this reissue specification; matter printed in italics indicates the additions made by reissue.

*Application Ser. No. 10/214,474 filed August 8, 2002 is a continuation application of the instant reissue application, Ser. No. 08/547,691, which application is, in turn, a continuation of application Ser. No. 07/890,280, filed May 29, 1992, now abandoned, which is a Reissue of Ser. No. 07/299,895, filed Jan. 23, 1989, now U.S. Pat. No. 4,928, 688.*

BACKGROUND OF THE INVENTION

I. Field of the Invention

This invention pertains to medical devices, but more specifically, to a method for increasing the cardiac output of a patient suffering from congestive heart failure by stimulating the heart of the patient at multiple sites simultaneously.

II. Discussion of the Prior Art

Normally, impulses from the SA node affect contraction of the atria and then propagate to the AV node. The AV node, in turn, emits a second nerve impulse which affects contraction of the ventricles. These nerve impulses affect contraction, i.e., depolarization of the tissue of the heart, in a coordinated manner to circulate blood through the body. Cardiac pacers of the type herein described generally are useful for maintaining proper functional operation of a sick heart. Of many cardiac deficiencies which have in the past been diagnosed and treated, conduction difficulties have presented significant problems for which a pacer has been used for treatment. A particular conduction deficiency, known as AV branch block, inhibits the transfer of nerve impulses from the sinoatrial (SA) node to atrial-ventricular (AV) node. When a bundle block occurs, these nerve impulses are not properly transmitted from the SA node to the AV node and ventricles.

When this condition occurs, normal treatment is to employ a pacer which locks onto the rhythmic cycle of the atrial beating signal and supplies to the ventricles a stimulating impulse at a certain time thereafter to effect contraction of the ventricles. The time period between the occurrence of the atrial beat and the normal contraction of the ventricles is known as the A-V delay period. Generally, hemodynamic efficiency is somewhat dependent to the A-V delay period, thus the pacer must emit a stimulating pulse at a time to preserve an optimum A-V delay period.

Other forms of conduction deficiency, such as myocardial scarring and bundle branch block, cause slow conduction of nerve impulses, in which case, nerve impulses are indeed passed from the SA to the AV node, but in a time period which is slower than normal. The Q-R-S complex in this case would manifest itself in being very wide and hemodynamic efficiency also becomes lower than normal.

In each of the above-mentioned cardiac deficiencies, the heart does not contract in coordinated fashion. This uncoordinated movement increases depolarization time and reults in more inefficient pumping rather than a more coordinated and simultaneous ventricular depolarization. In essence, such conduction deficiencies result in asynchrony between the left and right ventricle.

Additionally, arrhythmias of the heart produce uncoordinated ventricular contraction that affects the hemodynamic efficiency of the heart. Specifically, the recent paper "Incomplete Filling and Incoordinate Contraction as Mechanisms of Hypotension During Ventricular Tachycardia in Man", published in Circulation, Vol. 68, No. 5, in 1983, describes that left ventricular function is severely disturbed by the disorganization of wall motion in hearts undergoing ventricular tachycardias. Moreover, it was found that hearts with impaired functions show profound reductions in pumping ability due to incoordinate contraction of the ventricles. It appears reasonable to believe, therefore, that any abnormal functioning heart that requires pacemaking or which has QRS widening will have a better hemodynamic efficiency if both ventricles are paced to contract in coordination with each other. There have been systems developed in the past employing a plurality of electrodes attached to the heart for effecting stimulation of a plurality of regions of the heart. For example, the Funke U.S. Pat. No. 3,937,226 discloses a cardiac electrical stimulation defibrillation system including a plurality of electrode terminals connected in a spaced relation on the heart. The electrodes, which provide stimulating and sensing, are each connected to amplifiers. The amplifiers are connected to electronic control circuit means configured to cause stimulation of all of the electrode terminals simultaneously in response to a sensed depolrization signal on the heart by at least one electrode terminal. In addition, the electronic control circuit is provided with a multivibrator means to synchronize the stimulation signal with the Q-R-S complex. Although Funke does teach the concept of simultaneous stimulation of a plurality of spaced electrodes, he does not disclose its specific use as a method of improving the cardiac output of patients suffering from congestive heart failure, nor does he discuss the specific placement of the electrodes about the heart.

The Rockland et al U.S. Pat. No. 4,088,140 discloses a similar system to Funke's although a specific use as a pacemaker is stated in the patent. Rockland, et al discloses a demand anti-arrythmia pacemaker including a plurality of sensing electrodes connected to the heart to sense ventricular depolarizations. Electronic circuitry is provided having two paths of operation. A first path provides stimulation to one area of the heart if depolarization of a naturally occurring heart beat fails to occur within a first predetermined time period. In this first path, it is stated that the circuitry acts as a pacemaker in the event of skipped natural heartbeats. A second path provides stimulation to a plurality of locations on the heart if a depolarization signal is sensed on the heart with a second predetermined time period. In this second path, it is stated that the circuitry acts as a synchronous multiple electrode pacemaker or a synchronous multiple electrode defibrillator. Although, one example of an electrode placed in the intraventricular section and others in a spaced relation on the heart ventricles is given, there are no teachings of the specific placement of the electrodes on the heart nor the improvement of cardiac output from a sick heart. In addition, the electrodes perform either stimulating or sensing, not both, therefore a large number of electrodes is required in this system.

The Tacker, Jr. et al and McCorkle U.S. Pat. Nos. 4,548, 203, 4,458,677 and 4,332,259, respectively, disclose the specific placement of an electrode in or around both left and right ventricles of the heart. The Tacker, Jr. et al patent discloses the placement of a catheter having one electrode in the right ventricle and another outside the heart and a third electrode placed on the left ventricle. The catheter electrodes, each being paired with the left ventricular electrode, are pulsed in sequence with a predetermined time separation resulting in uniform current density delivered to the heart. However, this pulsing scheme and configuration is disclosed for use in a ventricular defibrillation device and not for cardiac pacing to improve cardiac output wherein a more precise synchronization of stimulation signals with the Q-R-S complex is required.

The McCorkle, Jr. patents disclose the specific placement of an electrode in the right ventricle and another electrode in the coronary sinus surrounding the left ventricle for connection to a pacemaker. However, there is no specific technique disclose of providing stimulating signals to the electrodes to perform a pacemaking function.

In light of the above difficulties and shortcomings of the prior art, an objective of the present invention is to provide a cardiac pacer for increasing hemodynamic efficiency of a heart experiencing a conduction deficiency.

Another objective of the invention is to ensure a more coordinated and simultaneous ventricular depolarization of both left and right ventricles of the heart.

A yet further objective of this invention is to provide a cardiac pacer suitable for being implanted in a manner so as to impose a minimal surgical risk during implantation thereof.

A further objective of this invention is to provide a method and apparatus of separately sensing and stimulating each ventricle of the heart in order for effecting simultaneous contraction automatically of both ventricles of the heart to narrow the QRS complex of a failing heart and thereby cause an increase in blood pressure and cardiac output.

SUMMARY OF THE INVENTION

The method of the present invention involves a procedure for pacing of the heart in a particular way so as to improve its contraction pattern, and thereby augment the movement of blood through the heart. Patients suffering from severe congestive heart failure, which is found not to respond well to conventional drug therapy and to have a conduction defect in the ventricle resulting in a widen Q-R-S complex have been aided by a pacing regimen in which stimulating pulses are simultaneously applied to both ventricles by way of a demand pacemaker or asynchronous pacemaker.

It is theorized that a considerable part of the hemodynamic impairment in refractory congestive heart failure with conduction defects is due to an incoordinate contraction of the heart, so that a part of the heart muscle contracts and balloons out the part that is not contracting. When the latter area of the heart muscle does finally contract, the former has relaxed, so that a large part of the blood volume is merely shunted back and forth within the heart rather than being ejected as would happen with a more coordinate contraction pattern.

To attain the foregoing and other objectives, the present invention comprises, a bi-ventricular cardiac pacer having detecting and stimulating circuits for effecting substatially simultaneous contraction of both left and right ventricles of the heart. In the preferred embodiment, the bi-ventricular pacer comprises ECG amplifier means for separately processing sensed cardiac signals from each of the right and left ventricles. The amplified sensed signals are used to determined where possible abnormal conduction delays exist on the heart and to activate an electrical stimulator for stimulating the appropriate abnormally functioning part of the heart. More specifically, the stimulator responds to the control circuit to issue stimulating pulses simultaneously to either the left or right ventricle, as appropriate. The stimulator may be of the demand type wherein pacing pulses are only issued in the absence of a normal Q-R-S complex for on or the other of the two ventricles (e.g., occasional bundle branch block or slow conduction), or the nondemand type wherein pacing pulses are always issued (e.g., permanent bundle branch block or slow conduction).

To convey and sense signals to and from the heart, the present invention includes a pacing lead assembly comprising first and second separate electrodes. The first electrode is preferably introduced through the superior vena cava into the right ventricle and the second electrode is introduced through the coronary sinus to the left ventricle. Both lead segments include a sensing and pacing tip electrode which serves to both sense a cardiac depolarization signal or to apply a stimulating pulse from an implanted pulse generator to the ventricle.

Additionally, to preserve a predetermined A-V delay period, additional atrial sensing electrodes may be placed on or around the atrial chambers of the heart and connected to the control circuit. The control circuit responds to the sensed atrial and ventricular depolarization signals to provide simultaneous ventricular contraction signals applied to the left and right ventricles following a preset A-V delay period.

The advantages of the present invention include a more precise and coordinated simultaneous ventricular depolarization of both the right and left ventricular to thereby increase hemodynamic efficiency of a patient experiencing congestive heart failure or weak contractions.

These together with other objects and advantages which will become subsequently apparent reside in the details of construction and operation as more fully hereinafter described and claimed, reference being had to the accompanying drawing forming a part hereof, wherein like numerals refer to like parts throughout.

BRIEF DESCRIPTION OF THE DRAWING FIGURES

Figure 2:
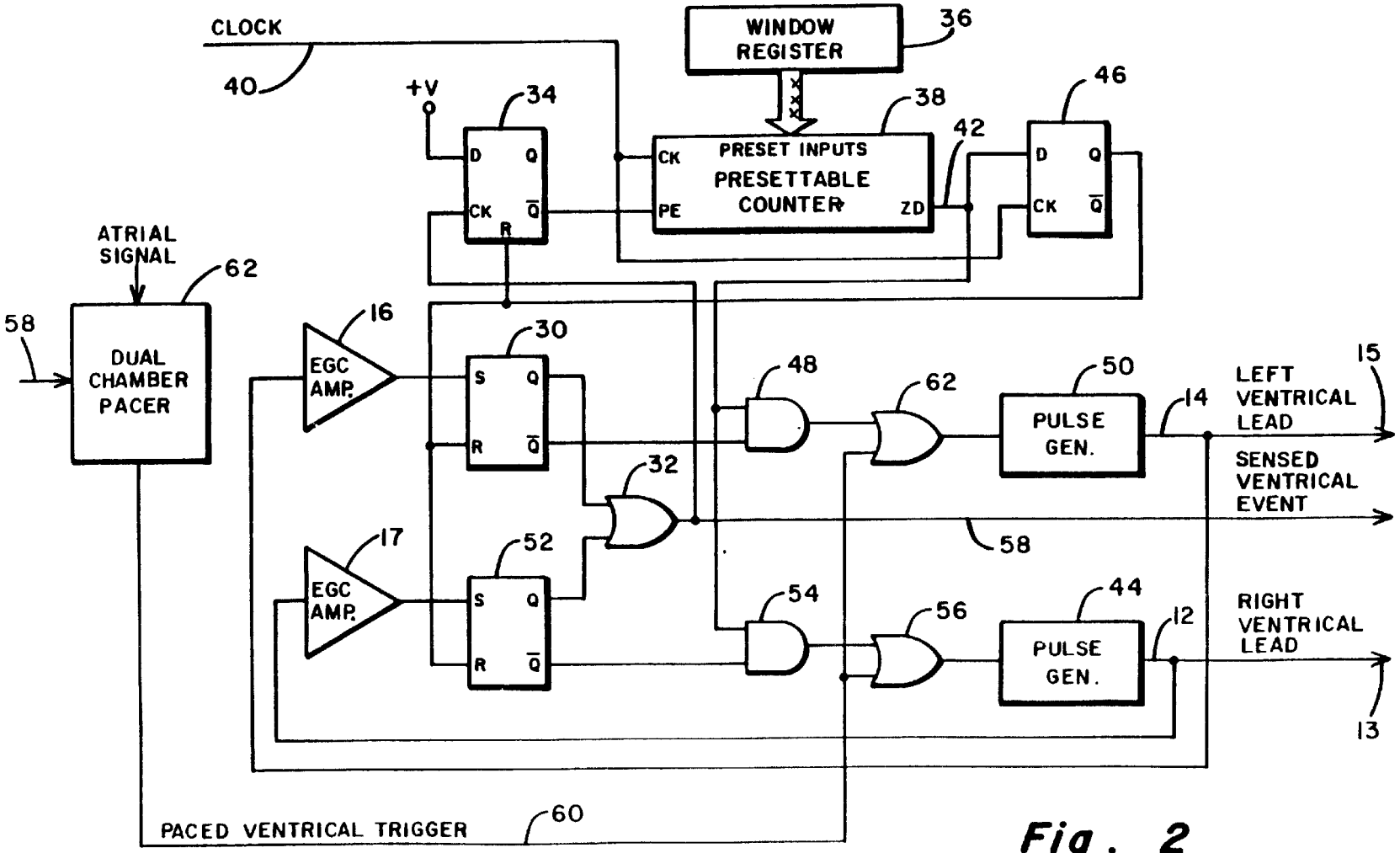

FIG. 1 depicts a functional block diagram of an apparatus for carrying out the teaching of this invention; and FIG. 2 is a logic diagram of the "CONTROL" shown in FIG. 1.

DETAILED DESCRIPTION OF THE PREFERRED EMBODIMENT

FIG. 1 illustrates the overall pacing system which may be employed for carrying out the teachings of the invention. A pair of leads 12 and 14 with corresponding sensing/stimulating tip electrodes 13 and 15 are electrically connected, via conductors 18 and 21, to separate ECG sense amplifiers 16 and 17 (or to a single multiplexed amplifier). The amplifiers 16 and 17 are both connected to a control circuit unit 20. A stimulator circuit 22 is connected to the control unit 20 and has two output conductor lines 24 and 26 which are electrically connected to the conductors 18 and 21, respectively. From this structure, signals my be separately sensed by the electrodes 13 and 15 and stimulating pacing signals may be separately delivered to the electrodes 13 and 15, via lead branches 12 and 14.

In operation, the electrodes 13 and 15 are disposed in or about the right and left ventricles, respectively. A preferred surgical procedure for implanting the lead 12 is to extend it through the superior vena cava 28 so that the sensing stimulating tip 13 thereof lodges in the internal chamber of the right ventricle of the heart 10. A preferred surgical procedure for implanting lead branch 14 is to extend it through the coronary sinus (not shown) of the heart 10 so that the sensing/stimulating tip 15 thereof lodges directly in or about the coronary simus and left ventricle. Although it is described that electrodes 13 and 15 perform both sensing and pacing, it is possible for testing and examination, that separate unipolar or bipolar sensing and stimulating electrodes may be used.

When attached to the heart, the electrodes 13 and 15 sense cardiac signals in the form of well-known Q-R-S complex at separate sites with the left and right ventricles. The ECG amplifiers 16 and 17 feed the amplified versions of these signals to the control circuit 20.

The control circuit 20 analyzes the cardiac signals to determine whether an abnormal conduction exists. Specifically, if a cardiac signal is received from the left ventricle but not from the right ventricle, the control circuit 20 provides a control signal to the stimulator 22 to issue a stimulating pacing pulse over conductors 24 and 18 and lead branch 12 to the right ventricle, via the sensing/stimulating tip electrodes 13. Similarly, the control circuit 20 provides a control signal to the stimulator 22 to issue a stimulating pacing pulse over lead branch 14 to the left ventricle, via sensing/stimulating tip electrode 15, if a cardiac depolarization signal is received from the right ventricle, but not from the left ventricle. It is also possible to sense a depolarization signal from only one ventricular chamber and then unconditionally stimulate both ventricular chambers. This is wasteful of powe which is a concern only if the stimulator is totally implanted and must rely on an implanted battery power source.

The timing of the stimulating pacing pulse from the stimulator 22 is such that both ventricles will contract substantially simultaneously. Where both ventricles are unconditionally stimulated upon the occurrence of a QRS complex on only one side, the fact that ventricular site which had produced a Q-R-S complex is immediately stimulated along with the other ventricle does not cause a problem since the site producing that complex is still refractory at the time it is stimulated.

It is also possible that no cardiac signals are sensed from either ventricle, possibly resulting from complete conduction failure between the sinoatrial node and the atrialventricular node. In this case, the control circuit 20 will again activate the stimulator 22 to provide stimulating signals to both ventricles simultaneously.

In an alternative embodiment of this invention, the issuance of pacing pulses to the ventricles is time-coupled to the rhythmic cycle of the atrial beat of the heart to preserve a preset atrial-ventricular delay period of about 120 to 200 milliseconds. Additional atrial sensing is accomplished, via lead 23 and a sense electrode 25 similar to the ventricular leads 12 and 14, but disposed in or about the right atrial chamber and connected to the control circuit 20, via atrial sense amplifier 27. The control circuit 20 may be configured to respond to the sensed atrial and ventricular signals to activate the stimulator for providing appropriate simultaneous stimulating signals to the ventricles as described above in accordance with the predetermined A-V delay period.

In the case where the conduction of the natural stimulating signal originating at the sinoatrial node of the heart 10 is only partially blocked or slowed, the ventricles may partially or incompletely contract, in which case hemodynanmic efficiency is reduced. Under these circumstances, provision is made in the control circuit 20 for determining whether a Q-R-S cardiac signal, although present, is weak or slow, and if so, to activate the stimulator 22 to stimulate the ventricles of the heart by passing pacing pulses simultaneously thereto.

FIG. 2 shows one embodiment of the control circuitry 20 of FIG. 1 required to perform bi-ventricular pacing. Also shown in the circuit of FIG. 2 are means for interconnecting the bi-ventricular control circuitry with conventional demand pacing circuitry to implement various additional pacing modes. It is understood that in the preferred embodiment, the circuitry shown in FIG. 1 would be preferably incorporated directly into the design of a pacer rather than its adjunctive form shown here for purposes of illustration.

To accomplish bi-ventricular pacing, activity is sensed in both the left and the right ventricle. When a ventricular contraction is sensed in either ventricle, a timer is initiated. If within a time window established by said timer, the contraction is sensed in the other ventricle, all pacing is inhibited because the natural contractions are deemed to be simultaneous. On the other hand, if ventricular contractions are not sensed in both ventricles within a period of coincidence defined by the time delay, at the end of this delay, the pacing pulse will be emitted, but only to the ventricle for which a QRS complex has not been sensed. Generally, ventricular contractions which occur with 5–10 milliseconds of each other result in sufficient hemodynamic efficiency so as to not require treatment. Hence, the delay window may be of this order of magnitude. As used herein, the term "substantially simultaneous contraction" includes the occurence of natural contractions of both ventricles with the window period or an evoked contraction of one or both ventricles immediately following the expiration of the window period.

Operation of the circuit of FIG. 2 will now be described. Electrical activity originating in the left ventricle is sensed by electrode 15 on lead 14 coupled to amplifier 16. It is assumed that amplifier 16 contains all of the thresholding and inhibiting provisions commonly utilized in existing pacing systems to inhibit all electrical activity, save valid ventricular contractions. Similarly, electrical activity in the right ventricle is sensed by electrode 13 on lead 12 and processed by ECG amplifier 17.

Let if first be assumed that a left ventricle contraction procedes that of the right. In this case, an R-wave signal propagates through amplifier 16 to set the Set-Reset type flip-flop 30. a logical "l" signal passes through OR gate 32 to clock D-type of flop 34 to the "set" state which, in turn, initiates the aforementioned delay timing. Window register 36 is loaded with a digital count value which is representative of the desired delay window, e.g., 5–10 ms. This may be either a fixed, hard-wired register or, alternatively, a programmable register which may be set by telemetry means in a known manner. When the preset enable input (PE) in high, counter 38 is held at a digital count corresponding to the value held in window register 36. When flip-flop 34 is set, the PE on counter 38 is removed, allowing the counter to be decremented with each clock pulse provided on clock line 40. At the end of the preporgrammed window delay interval, counter 38 is decremented to zero, causing the zero detect (ZD) line 42 to go high. The leading edge of the zero detect pulse is used to trigger a ventricle pacing pulse from pulse generator 44, via gates 54 and 56, as required. The pulse generator circuitry 44 converts the leading edge trigger to a pulse of the proper amplitube and duration for effective stimulation of the right ventricle. Note that, since under the assumed conditions flip-flop 30 has been set, AND gate 48 is disabled and, therefore, pulse generator 50 is inhibited from generating a left ventricle pacing pulse.

Next to be considered is the case where a right ventricle contraction has not been sensed within the prescribed window interval. In this case, flip-flop 52 remains reset and AND gate 54 is enabled which allows the zero detect pulse ZD to propagate through OR gate 56 to trigger pulse generator 44, thus stimulating the right ventricle. If, however, a right ventricle contraction has been detected, flip-flop 52 would have been set prior to the generation of the ZD pulse and, in this case, both AND gates 48 and 54 are disabled and no pacing pulse in either ventricle is generated.

It can be seen from the symmetry of the circuit that the operation is identical if the right ventricle contraction precedes the left ventricle contraction by more than the preprogrammed delay interval. In either case, the setting of either flip-flop 30 or 52 causes 52 causes the initiation of the timing window delay interval. When one of these flip-flop sets, the other must set within the window period, otherwise a pacing pulse will be generated in the unsensed ventricle.

The vi-bentriclar pacing control circuitry may be combined with other well-known pacer control circuitry such that the bi-ventriclar mode can be realized in combination with any other pacing mode, such as VVI, DDD, VOO. Line 58 is the logical OR of either of left ventricle event or a right ventricle event. It may be connected to other pacing control circuitry 62 in place of the signal which is normally responsive to only activity in the left ventricle. A sensed ventricle event thus inhibits the generation of a pacing trigger from another pacing circuitry and leaves the control of pacing in the alternate ventricle, as required; to the circuitry of FIG. 1. If line 58 is not activated within the escape interval of the other pacing control circuitry, a paced ventricle trigger signal on line 60 is produced which propagates through both OR gate 62 and OR gate 56 to trigger pacing pulses in both ventricles.

It is also contemplated that when a ventricular depolarization signal is sensed in one or the other of the ventricles, that a stimulating pulse may also be immediately delivered, on an unconditional basis, to both ventricles, via the implanted leads 13 and 15, thus resulting in a coordinated contraction of both ventricles.

The foregoing illustrate preferred arrangements for carrying out the objectives of this invention. Modifications and variations can obviously be made by those skilled in the art without departing from the true spirit and scope of the invention. For instance, the circuit may be employed to simultaneously pace the auricles, instead of ventricles, if such is required to improve pumping efficiency. The arrangement may also be employed as an improvement of conventional pacers thereby to improve their performance. As stated herein, the inventive arrangement can be used in an implanted device or in an external treating, diagnostic or testing device. Accordingly, the invention is limited only by the scope of the appended claims rather than by what is shown and described. Therefore, it is the intent to cover all such modifications and alternate embodiments as may come within the true scope of this invention.

What is claimed is:

1. A method for improving the hemodynamic efficiency of a sick heart comprising the steps of:

(a) detecting respective cardiac signals originating in the left and right ventricles of the heart;

(b) analyzing said cardiac signals and the absence thereof in an electronic control circuit; and (c) providing electrical pulses from a stimulating circuit controlled by said control circuit to one, the other or both ventricles as required for effecting substantially simultaneous contraction of both ventricles, said step of analyzing including providing a control signal from said control circuit to said stimulating circuit for producing an electrical stimulating pulse to one or both ventricles in response to the absence of a detected cardiac signal from one or both ventricles within a time interval which is a small fraction of the pulse width of a detected cardiac signal.

2. The method of claim 1 wherein said step of detecting respective cardiac signals comprises deposing electrodes in or on the left and right ventricles for separately detecting the respective cardiac signals of the left and right ventricles, and applying said cardiac signals to separate ECG amplifier means connected to each of said electrodes to amplify the cardiac signal for analysis.

3. The method of claim 2 wherein said step of providing electrical pulses includes delivering an electrical pulse from said stimulating circuit to said electrodes in or on both the left and right ventricles.

4. The method of claim 1 wherein said step of analyzing further includes providing a control signal from said control circuit to the stimulating circuit to produce an electrical stimulating pulse to the left ventricle in the absence of a detected cardiac signal from the left ventricle, or to the right ventricle in the absence of a detected cardiac signal from the right ventricle, or to both ventricles in the absence of detected cardiac signals from both ventricles.

5. A method for effecting simultaneous contraction of both left and right ventricles of a heart for improving hemodynamic efficiency comprising the steps of:

separately sensing for the presence of cardiac depolarization signals from both left and right ventricles;

determining whether said cardiac depolarization signals are simultaneously present in both the left and right ventricles; and stimulating at least one ventricle substantially simultaneously with the contraction of a least one other ventricle in the event that said cardiac depolarization signals are determined not to be simultaneously present in both ventricles.

6. A method of effecting simultaneous contraction of both left and right ventricles of a heart for improving hemodynamic efficiency comprising the steps of:

sensing the cardiac signals of the atria and separately sensing the cardiac depolarization signals of both the left and right ventricles;

determining whether said cardiac depolarization signals are simultaneously present in both the left and right ventricles;

stimulating at least one ventricle simultaneously with the contraction of at least one other ventricle after a predetermined A-V period in the event that said cardiac depolarization signals are determined not to be simultaneously present in both ventricles.

7. A method of increasing the cardiac output of a sick heart comprising the steps of:

(a) implanting a pacing lead having at least two sensing/pacing electrodes in the body such that one of said sensing/pacing electrodes is in or on the right ventricle and the other of said sensing/pacing electrodes is in or on the left ventricle;

(b) sensing depolarization signals picked up by said sensing/pacing electrodes upon their occurrence;

(c) determining whether the depolarization signals sensed in step (b) fail to occur within a predetermined time interval of one another and, if so;

(d) applying an electrical stimulating pulse to the sensing/pacing electrode associated with the ventricle not producing a depolarization signal within said time interval at the conclusion of said time interval.

8. The method as in claim 7 wherein said predetermined time interval is in the range of from about 5 ms. to 10 ms.

9. A bi-ventricular pacemaker, comprising:

(a) sense means for sensing ventricular depolarization signals originating in or on the right and left ventricles;

(b) means coupled to said sense means for initiating a time delay of a predetermined length which is short compared to the period of a QRS complex upon detection of a ventricular depolarization signal in one of said right or left ventricles; and (c) pulse generator means operative upon the termination of said time delay for producing a ventricular simulating pulse and applying same to the other of said right or left ventricles unless a ventricular depolarization signal occurs in said other of said right or left ventricle prior to the expiration of said time delay.

10. The bi-ventricular pacemaker as in claim 9 wherein said sense means comprises a bi-ventricular lead having a first electrode for contacting the left ventricle and sense amplifier means electrically coupled to said first and second electrodes.

11. The bi-ventricular pacemaker as in claim 10 wherein said means coupled to said sense means includes:

(a) first and second set-reset flip-flop connected to be set by an output from said sense amplifier means;

(b) presetable counter means for initially containing a digital value representative of said time delay;

(c) means for incrementing or decrementing said digital value in said presettable couter means at regular intervals until a predetermined count is reached;

(d) means responsive to the value in said counter means reaching said predetermined count for producing a control signal;

(e) logic means coupled to said first and second flip-flops and to said presettable counter means for receiving said control signals; and wherein (f) said pulse generator means is enabled by said logic means.

12. The bi-ventricular pacemaker as in claim 11 wherein said pulse generator means is coupled to said first and second electrodes.

13. An atrial-coupled, bi-ventricular pacemaker for implantation or external use comprising atrial and ventricular sensing means for detecting cardiac signals, said sensing means including first and second ventricular electrodes connected in series for sensing and stimulating the right and left ventricles, respectively, and an atrial electrode adapted to be disposed in an atrial chamber for detecting cardiac signals of the atria, all of said electrodes being connected to separate ECG amplifier means for amplifying the sensed signals; a control circuit coupled to said ECG amplifier means for analyzing the cardiac signals picked up by said sensing means and providing a control signal; and a stimulating circuit means for producing an electrical stimulating pulse to the left ventricle in the absence of a detected cardiac signal from the left ventricle, and to the right ventricle in the absence of a detected cardiac signal from the right ventricle, and to both ventricles in the absence of detected cardiac signals from both ventricles to effect substantially simultaneous contraction of both ventricles after a predetermined A-V delay period.

14. The pacemaker of claim 13 wherein said first electrode is adapted to be placed in the right ventricle and the second electrode is adapted to be placed in the coronary sinus extending about the left ventricle.

*15. A method for improving the hemodynamic efficiency of a heart comprising the steps of:*

*detecting a cardiac depolarization signal originating from a first ventricle;*

*immediately and unconditionally stimulating both ventricles for effecting a coordinated contraction of both ventricles when a cardiac depolarization signal originating from the first ventricle is detected.*

*16. The method of claim 15 wherein the step of immediately and unconditionally stimulating both ventricles further comprises providing electrical pulses from a stimulating circuit to both ventricles.*

*17. The method of claim 16 wherein said step of detecting a cardiac depolarization signal further comprises positioning electrodes in or about both ventricles for detecting cardiac depolarization signals and for conducting a signal to an electronic control circuit for controlling the stimulating circuit.*

*18. The method of claim 17 wherein said step of detecting a cardiac depolarization signal further comprises conducting the signal to an amplifier means to amplify the detected signal, and applying the amplified signal to the control circuit.*

*19. A method for improving the hemodynamic efficiency of a heart comprising the steps of:*

*sensing a contraction of the atria; and*

*stimulating both ventricles for effecting a coordinated contraction of both ventricles when a contraction of the atria is sensed and following a predetermined A-V delay period.*

*20. The method according to claim 19, further comprising, before said sensing step:*

*placing a first electrode into the right ventricle through the superior vena cava and placing a second electrode into the left ventricle through the coronary sinus;*

*wherein said stimulation of both ventricles is an electrical discharge through said first and second electrode.*

*21. The method according to claim 19, further comprising, before said sensing step:*

*placing a pair of sensing and pacing tip electrodes into each of the right and left ventricles;*

*wherein said sensing is detected through said pair of sensing tip electrodes.*

*22. A bi-ventricular pacemaker, comprising:*

*sense means for sensing ventricular depolarization signals originating from one of left and right ventricles; and*

*pulse generator means operative upon sensing a depolarization signal from the one of the ventricles for producing a stimulating pulse and immediately and unconditionally applying the stimulating pulse to both ventricles.*

*23. A bi-ventricular pacemaker according to claim 22, wherein the sense means includes a lead having a first electrode for placement in or about the left ventricle and a second electrode for placement in or about the right ventricle.*

*24. A bi-ventricular pacemaker according to claim 22, wherein the pulse generator means includes a sense amplifier means electrically coupled to the first and second electrodes for amplifying a sensed depolarization signal, a stimulating circuit for producing the stimulating pulse, and a control circuit operative to control the stimulating circuit in response to the amplified sensed depolarization signal.*

*25. A bi-ventricular pacemaker comprising:*

*detecting means for detecting a cardiac signal resulting from a contraction of a first ventricle;*

*stimulating means for effecting immediate and unconditional contraction of a second ventricle in response to the detected cardiac signal, thereby effecting simultaneous contraction of both ventricles.*

*26. A bi-ventricular pacemaker according to claim 25 further comprising stimulating means for providing a stimulating pulse to the first ventricle simultaneous with the effecting of the immediate and unconditional contraction of the second ventricle.*

* * * * *

UNITED STATES PATENT AND TRADEMARK OFFICE

CERTIFICATE OF CORRECTION

PATENT NO. : RE 38,119 E
DATED : May 20, 2003
INVENTOR(S) : Morton M. Mower

It is certified that error appears in the above-identified patent and that said Letters Patent is hereby corrected as shown below:

Column 8,
Line 35, “of a least” should read -- of at least --.

Column 9,
Lines 19-20, “a first electrode for contacting the left ventricle” should read -- a first electrode for contacting the right ventricle and a second electrode for contacting the left ventricle --.
Line 31, “couter” should read -- counter --.

Signed and Sealed this

Twenty-third Day of March, 2004

JON W. DUDAS
*Acting Director of the United States Patent and Trademark Office*